US011197786B2

(12) United States Patent
Kuramochi

(10) Patent No.: US 11,197,786 B2
(45) Date of Patent: Dec. 14, 2021

(54) ABSORBENT ARTICLE

(71) Applicant: DAIO PAPER CORPORATION, Ehime (JP)

(72) Inventor: Mihoko Kuramochi, Tochigi (JP)

(73) Assignee: DAIO PAPER CORPORATION, Ehime (JP)

(*) Notice: Subject to any disclaimer, the term of this patent is extended or adjusted under 35 U.S.C. 154(b) by 337 days.

(21) Appl. No.: 16/070,631

(22) PCT Filed: Jan. 24, 2017

(86) PCT No.: PCT/JP2017/002355
§ 371 (c)(1),
(2) Date: Jul. 17, 2018

(87) PCT Pub. No.: WO2017/130964
PCT Pub. Date: Aug. 3, 2017

(65) Prior Publication Data
US 2019/0282414 A1 Sep. 19, 2019

(30) Foreign Application Priority Data
Jan. 26, 2016 (JP) .............................. JP2016-011996

(51) Int. Cl.
*A61F 13/47* (2006.01)
*A61F 13/511* (2006.01)
(Continued)

(52) U.S. Cl.
CPC ........ *A61F 13/51108* (2013.01); *A61F 13/47* (2013.01); *A61F 13/472* (2013.01);
(Continued)

(58) Field of Classification Search
CPC ................ A61F 13/4704; A61F 13/472; A61F 13/47218; A61F 13/47236;
(Continued)

(56) References Cited

U.S. PATENT DOCUMENTS

2012/0265162 A1\* 10/2012 Kuramochi ......... A61F 13/4758
604/385.101
2016/0143790 A1\* 5/2016 Umemoto ............... A61F 13/45
604/372

FOREIGN PATENT DOCUMENTS

EP 2517682 10/2012
JP 2007-014635 1/2007
(Continued)

OTHER PUBLICATIONS

International Search Report for PCT/JP2017/002355 dated Apr. 25, 2017.
(Continued)

*Primary Examiner* — Catharine L Anderson
(74) *Attorney, Agent, or Firm* — IPUSA, PLLC

(57) ABSTRACT

A compressed groove point (16) where compressed grooves (12) formed bilaterally and symmetrically on both sides of a center line (CL) in a lengthwise direction of a sanitary napkin (1) or lines extended from center lines of the compressed grooves (12) intersect with each other at a position corresponding to a front end (31) of a intergluteal cleft of a wearer is formed, and a right and left pair of outline inflection points (17) is formed in an outline of a rear end of the sanitary napkin (1) formed into a bilateral and symmetric wavelike shape. Easy deformation parts (18) that facilitate generation of a deformation in a transverse direction of the sanitary napkin (1) and are formed of the compressed grooves that become base edges of the deformation, are provided on or in the vicinity of two virtual lines (S) connecting the compressed groove base point (16) to the outline inflection points (17) on right and left sides, respectively, such that a distance between the two virtual lines (S) gradually increases toward a rea side.

6 Claims, 4 Drawing Sheets

(51) Int. Cl.
*A61F 13/472* (2006.01)
*A61F 13/533* (2006.01)

(52) U.S. Cl.
CPC .. *A61F 13/47218* (2013.01); *A61F 13/47236* (2013.01); *A61F 13/533* (2013.01)

(58) Field of Classification Search
CPC .......... A61F 13/51104; A61F 13/51108; A61F 13/533; A61F 2013/4706
USPC ................................................ D24/124–126
See application file for complete search history.

(56) References Cited

FOREIGN PATENT DOCUMENTS

| | | |
|---|---|---|
| JP | 2011-172658 | 9/2011 |
| JP | 2014-036832 | 2/2014 |
| JP | 2015-167773 | 9/2015 |
| WO | WO-2014208729 A1 * 12/2014 | ......... A61F 13/5323 |

OTHER PUBLICATIONS

Extended European search report for European Patent Application No. 17744194.6 dated Nov. 7, 2018.

* cited by examiner

ABSORBENT ARTICLE

TECHNICAL FIELD

The present invention relates to an absorbent article such as a sanitary napkin, a panty liner, an incontinence pad, and a disposable diaper for absorbing body fluids such as menstrual blood, vaginal discharge, and urine and specifically, relates to an absorbent article having a protruding part that fits a intergluteal cleft formed by deforming compressed grooves formed in a surface and an outline of a rear end of the absorbent article while associating the compressed grooves with the outline of the rear end of the absorbent article.

BACKGROUND ART

Conventionally, as absorbent articles such as panty liners, incontinence pads, and sanitary napkins, a structure is known that has an absorbent body made of cotton-like pulp between a liquid impermeable backsheet such as a polyethylene sheet or a polyethylene-sheet-laminated non-woven fabric and a liquid permeable topsheet such as a non-woven fabric or a liquid permeable plastic sheet.

Such types of absorbent articles have been enhanced many times, and a variety of measures to prevent body fluids and the like from leaking by causing the absorbent articles to closely contact with the body, has been performed. For example, there is a technique of forming a compressed groove in a top side by heat embossing in order to enhance fitness of the absorbent body to the intergluteal cleft by causing a rear part of the absorbent article to protrude, and in order to prevent the body fluid from spreading by preventing twists of the absorbent body.

For example, an absorbent article disclosed in the following Patent Document 1 has one compressed groove and the other compressed groove that constitutes a pair of compressed grooves formed in a topsheet side at a rear portion, and the compressed groves are symmetrically formed with respect to a longitudinal center line of the absorbent article and are apart from each other in a lateral direction. The compressed grooves have a curved shape that is convexly curved rearward in the longitudinal direction in a planar view, and is structured by including a curved portion that forms a peak of the curve, an inner line, and an outer line. The inner line and the outer line each extend along tangent lines at ends of the curved portion to which the inner line and the outer line are coupled, and the distance between the inner line of one compressed groove and the inner line of the other compressed groove decreases toward the front side in the longitudinal direction while the distance between the outer line of one compressed groove and the outer line of the other compressed groove increases toward the front side in the longitudinal direction in the pair of compressed grooves. Thus, Patent Document 1 discloses the absorbent article that has the longer outer lines in the longitudinal direction than the inner lines in the longitudinal direction, in the compressed grooves.

Moreover, the following Patent Document 2 discloses an absorbent article that has a plurality of lateral grooves extending in a width direction and provided at a predetermined pitch in a lengthwise direction.

RELATED-ART DOCUMENTS

Patent Document

Patent Document 1: Japanese Unexamined Patent Application Publication No. 2015-167773

Patent Document 2: Japanese Examined Patent Publication No. 4540563

SUMMARY OF THE INVENTION

Problem to be Solved by the Invention

The absorbent article described in the above-mentioned Patent Document 1 causes a distant portion between the pair of compressed grooves to deform so as to protrude toward a skin facing side along the longitudinal direction by providing the pair of compressed groves, thereby being fitted to the intergluteal cleft of a wearer. However, because there has been no base point that becomes a front end of the protruding deformation in the longitudinal direction (lengthwise direction), the front end of the deformation has not been able to fit an end of a groin side of the buttock cleavage (front end of the intergluteal cleft) of the wearer. Because of this, if the front end of the protruding deformation is formed on the front side of the front end of the intergluteal cleft of the wearer, a portion at and around the front end of the protruding deformation is away from the skin surface, which impairs the fitness. On the other hand, if the front end of the protruding deformation is formed on the rear side of the front end of the intergluteal cleft, the fitness is impaired because the absorbent article does not go into the front end of the intergluteal cleft. Accordingly, there has been a problem of increasing a concern of causing a body fluid leakage traveling along the skin in either case.

Furthermore, the absorbent article described in the above-mentioned Patent Document 1, because the outline of the rear end of the absorbent article is formed as a monotonous arc that is convexly curved rearward, when the distant portion between the compressed groves is deformed so as to protrude toward the surface opposite to the skin along the longitudinal direction, the rear end of the protruding deformation has been sometimes unlikely to deform depending on a shape of the outline of the rear end of the absorbent article. This has generated twists and wrinkles at the rear end of the protruding deformation, and caused a problem of degrading the wearing comfort when being fitted to the intergluteal cleft of the wearer.

In addition, in the above-mentioned Patent Document 2, by providing a plurality of lateral grooves extending in a width direction in an upper surface side of the absorbent body, the absorbent body is likely to bend in a lengthwise direction due to the lateral grooves that serves as a flexible axis. However, on the other hand, there has been a problem of being unlikely to generate a chevron protruding deformation that has its peak at the center in the width direction with respect to the transverse direction of the absorbent article. Due to this, there has been a problem of making the protruding deformation part unlikely to go into the intergluteal cleft when being worn, thereby degrading the fitness because of a gap between the skin surface and the protruding deformation part, and the wearing comfort.

Therefore, the principal purpose of embodiments of the present invention is to provide an absorbent article that readily fits the intergluteal cleft and has preferable wearing comfort.

Means to Solve the Problem

In order to solve the above described problem, an absorbent article includes a liquid permeable topsheet having compressed grooves in a surface, a backsheet, and an absorbent body interposed between the liquid permeable topsheet and the backsheet. A compressed groove point where the compressed grooves formed bilaterally and symmetrically on both sides of a center line in a lengthwise direction of the absorbent article or lines extended from center lines of the compressed grooves intersect with each other at a position corresponding to a front end of a intergluteal cleft of a wearer is formed, and a right and left pair of outline inflection points is formed in an outline of a rear end of the absorbent article. The outline of the rear end is formed into a bilateral and symmetric wavelike shape. Easy deformation parts that facilitate generation of a deformation in a transverse direction of the absorbent article and are formed of the compressed grooves that become base edges of the deformation, are provided on or in the vicinity of two virtual lines connecting the compressed groove base point to the outline inflection points on right and left sides, respectively, such that a distance between the two virtual lines gradually increases toward a rear side. The compressed grooves are made base edges of the deformation.

Advantage of the Invention

As described above, according to the embodiments of the present invention, an absorbent article that readily fits the intergluteal cleft and has preferable wearing comfort.

MODE FOR CARRYING OUT THE INVENTION

In the following, embodiments of the present invention are described below with reference to the accompanying drawings.

[Basic Structure of Sanitary Napkin 1]

Figure 1:
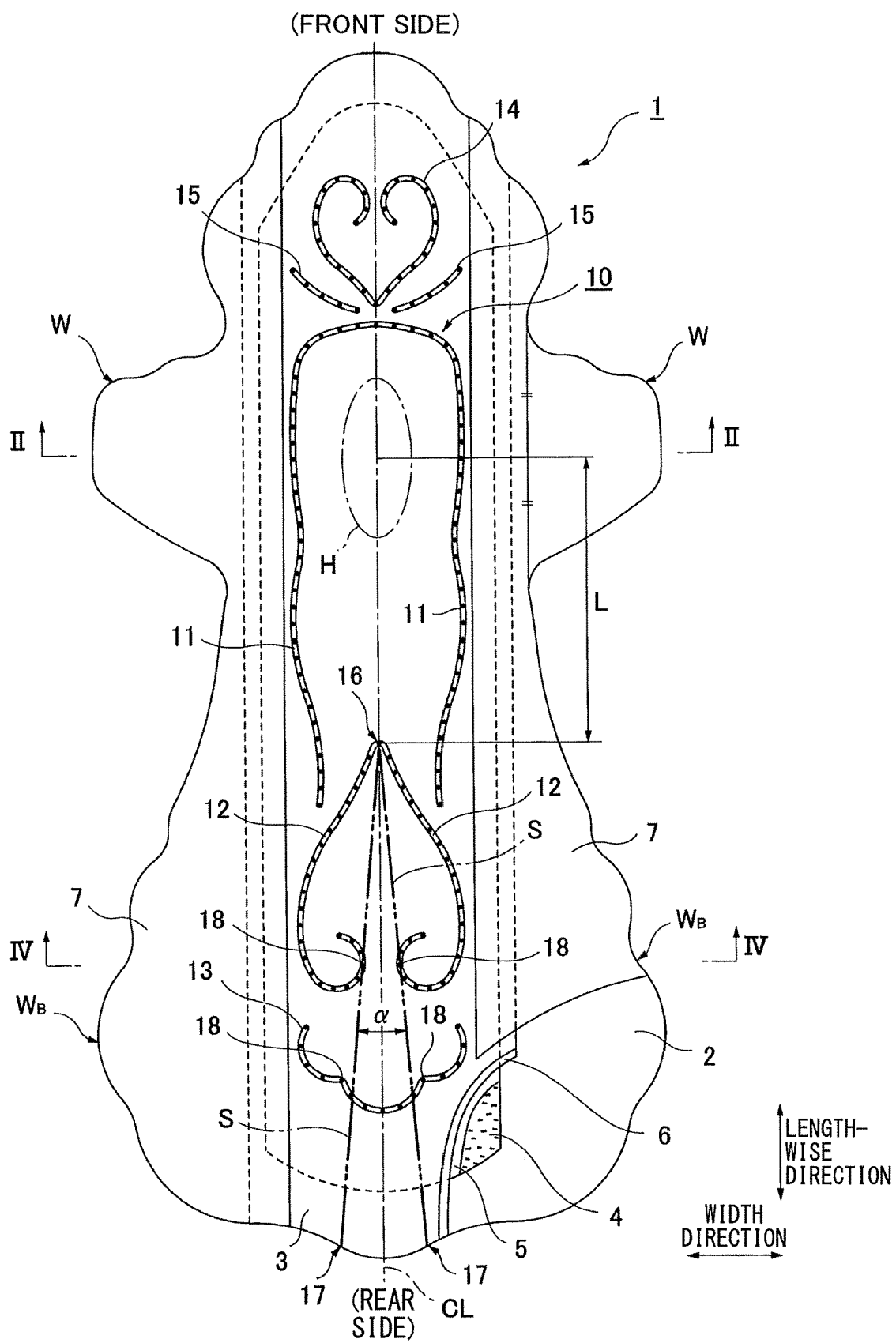
FIG. 1 is a partially broken development view of a sanitary napkin 1 according to the present invention.
Figure 2:
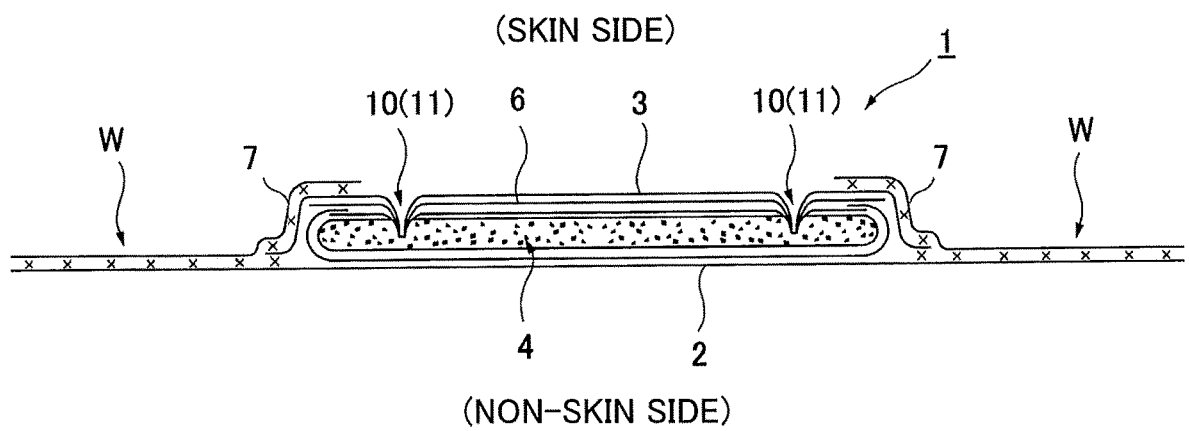
FIG. 2 is a cross-sectional view taken along a line II-II of FIG. 1.

As illustrated in FIG. 1 and FIG. 2, a sanitary napkin 1 according to the present invention includes a liquid impermeable backsheet 2 formed of a sheet such as a polyethylene sheet or a polypropylene sheet; a liquid permeable topsheet 3 that allows menstrual blood, vaginal discharge, and the like (which are hereinafter referred to as a body fluid) to quickly pass through; and an absorbent body 4 interposed between these sheets 2 and 3 and made of pulp, such as cotton-like pulp or synthetic pulp. Moreover, the sanitary napkin 1 includes an encapsulating sheet 5 that surrounds the absorbent body 4 and is made of crepe paper, non-woven fabric or the like to retain a shape of the absorbent body 4 and to enhance diffusivity of the absorbent body 4, a hydrophilic second sheet 6 disposed between the liquid permeable topsheet 3 and the absorbent body 4, and a side non-woven sheet 7 provided on both lateral sides of the skin contact surface side and along the lengthwise direction. Around the absorbent body 4, peripheral portions of the liquid impermeable backsheet 2 and the liquid permeable topsheet 3 are joined to each other by bonding means such as adhesive agent like a hot melt, a heat seal, and an ultrasonic sound wave seal at the periphery of a top end and a lower end of the absorbent body 4. Furthermore, on both peripheries of the absorbent body 4, the liquid impermeable backsheet 2 and the above-mentioned side non-woven fabric that laterally extend longer than the absorbent body 4 are joined to each other by an adhesive agent such as hot melt, heat seal, supersonic sound wave seal and the like, and stacked sheet parts of the liquid impermeable backsheet 2 and the side non-woven fabric 7 form wing-shaped flaps W, W that project laterally up to a location outside the absorbent body 4. Moreover, rear flaps $W_B$, $W_B$ are formed on the buttock side of the wing-shaped flaps W, W, and the sanitary napkin 1 is formed as a so-called nighttime napkin that covers a wide range of the buttock of the wearer and extends long backward.

Furthermore, the structure of the above-mentioned sanitary napkin 1 is described below. A sheet material having at least a water interception property such as olefin based resin sheet including polyethylene and polypropylene is used as the liquid impermeable backsheet 2. In addition to these, a laminated non-woven fabric sheet formed by stacking non-woven fabric in layers on the polyethylene sheet, a non-fabric sheet that substantially ensures the liquid impermeable property by further being covered with a waterproof film (in this case, the waterproof film and the non-woven fabric constitute the liquid impermeable backsheet) and the like, can be used as the liquid impermeable backsheet 2. In recent years, a material having moisture permeability is likely to be used to prevent dampness. This water shielding and permeable sheet material is a macroporous sheet obtained by stretching it in one axial direction or two axial directions after forming a sheet by melting and kneading an inorganic filler in olefin resin such as polyethylene and polypropylene.

Next, a non-woven fabric is preferably used for the liquid permeable topsheet 3. For example, a recycled fiber such as rayon or cupra, and a natural fiber such as cotton can be used as a material that forms the non-woven fabric in addition to a synthetic fabric such as an olefin based synthetic fabric including polyethylene and polypropylene, a polyester based synthetic fabric, a polyamide based synthetic fabric and the like. Moreover, a non-woven fabric obtained by appropriate processing methods such as a spun lace method, a spun bond method, a thermal bond method, a melt-blown method or a needle punch method can be used. Among these processing methods, the spun lace method has an advantage in terms of flexibility, the spun bond method has an advantage in terms of a doping property, and the thermal bond method and air through method has an advantage in terms of bulkiness and compression restorability. Further, a composite fiber may be used such as a core-in-sheath fiber including a high-melting-point fiber as a core and a low-melting-point fiber as a sheath, a side-by-side fiber, or a split fiber.

The absorbent body 4 interposed between the liquid impermeable backsheet 2 and the liquid permeable topsheet 3 is formed with, for example, cotton-like pulp and a highly water absorptive polymer. As the highly water absorptive polymer, a superabsorbent polymer granular powder (SAP) or a superabsorbent polymer fiber (SAF) may be used. Examples of the pulp described above include chemical pulp made from wood, cellulose fibers such as dissolving pulp and synthetic cellulose fibers such as rayon and acetate. In terms of the function and the price, softwood pulp with a long fiber length is more preferably used than hardwood pulp. For a method of producing the absorbent body 4, although fiber stacking pulp is preferably used for obtaining the desired flexibility, an air laid absorbent body may be used to reduce bulk. The absorbent body 4 may be surrounded by an encapsulating sheet (not illustrated) made of a crepe paper sheet or a nonwoven fabric in order to retain a shape and to improve diffusivity thereof.

Moreover, a synthetic fiber may also be mixed in the absorbent body 4. For the above-mentioned synthetic fiber, for example, a polyolefin fiber such as polyethylene or polypropylene; a polyester fiber such as polyethylene terephthalate or polybutylene terephthalate; a polyamide fiber such as nylon; and a copolymer of these polymers may be used. Also, a mixture of two types of these may be used. Further, a composite fiber may be used such as a core-in-sheath fiber including a high-melting-point fiber as a core and a low-melting-point fiber as a sheath, a side-by-side fiber, or a split fiber.

The hydrophilic second sheet 6, disposed as needed adjacent to the non-skin side of the liquid permeable topsheet 3, may be a sheet having a hydrophilic property with respect to a body fluid. Specifically, a sheet having a hydrophilic material using a regenerated fiber such as rayon or cupra or a natural fiber such as cotton can be used, or a fiber to which a hydrophilic property is added by applying, by use of a hydrophilizing agent, a surface treatment to a synthetic fiber such as an olefin fiber of polyethylene, polypropylene, or the like, a polyester fiber, or a polyamide fiber. Further, a composite fiber may be used such as a core-in-sheath fiber including a high-melting-point fiber as a core and a low-melting-point fiber as a sheath, a side-by-side fiber, or a split fiber.

It is preferable to join the second sheet 6 and the absorbent body 4 (encapsulating sheet 5) together through a hot melt adhesive agent or the like. By joining the second sheet 6 and the absorbent body 4, body fluids such as menstrual blood can be rapidly transferred from the second sheet 6 to the absorbent body 4.

[Regarding Compressed Grooves and Outlines of Rear End]

In the present sanitary napkin 1, components from the above-mentioned liquid permeable topsheet 3 to the absorbent body 4 are formed integrally by compression from a top surface side of the liquid permeable topsheet 3, and a compressed line 10 recessed toward the above-mentioned liquid impermeable backsheet 2 is formed bilaterally and symmetrically. The present sanitary napkin 1 features an association of the compressed groove 10 with an outline of a rear end of the napkin, thereby facilitating a deformation of the sanitary napkin 1 that fits a intergluteal cleft 30 (see FIG. 3). This configuration is specifically described below.

As illustrated in FIG. 1, the above-mentioned compressed groove 10 in the present sanitary napkin 1 includes bilaterally symmetric central-part compressed grooves 11, 11 that are provided along a lengthwise direction of the napkin on both sides so as to contain a body fluid discharge part corresponding region H and curve toward a center line CL in the lengthwise direction at a front end thereof so as to form into an approximately horseshoe shape that opens at a rear end as a whole, and a first rear compressed groove 12 that is arranged on the rear side of the above-mentioned central-part compressed groove 11, extends rearward therefrom, and has a reverse heart shape that has its base point on the center line CL in the lengthwise direction in a planer view. Moreover, the above-mentioned compressed groove 10 includes a second rear compressed groove 13 that is arranged on the rear side of the above-mentioned first rear compressed groove 12 and includes an arc that curves rearward on the center line Cl in the lengthwise direction and arcs that obliquely curve rearward on both sides thereof, a first front compressed groove 14 that is arranged on the front side of the above-mentioned central-part compressed groove 11 and has an approximately heart shape having its base point on the center line CL in a planar view, and a right and left pair of second front compressed grooves 15, 15 that are arranged between the central-part compressed groove 11 and the first front compressed groove 14 and are apart from each other on the right and left sides with respect to the center line CL in the lengthwise direction while curving rearward as a whole. Here, the shapes of the above-mentioned first front compressed groove 14 and the second front compressed groove 15 are not limited to a specific shapes, and may not be bilaterally symmetrical. Further, any one or both of the above-mentioned first front compressed groove 14 and the second front compressed groove 15 may not be provided, or another compressed groove may be further added.

Figure 3:
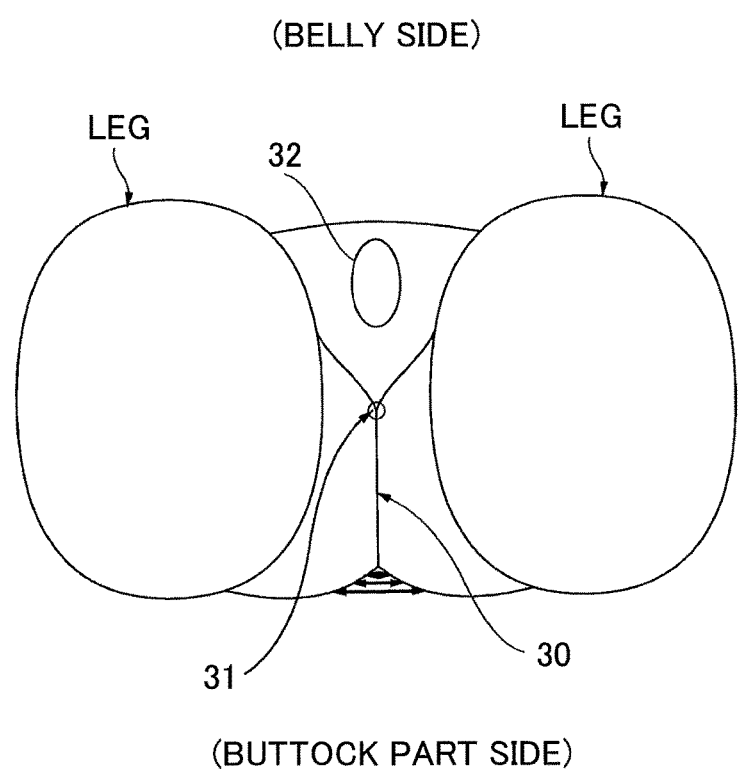
FIG. 3 is a schematic view of a groin part of a human body as seen from below.
Figure 4:
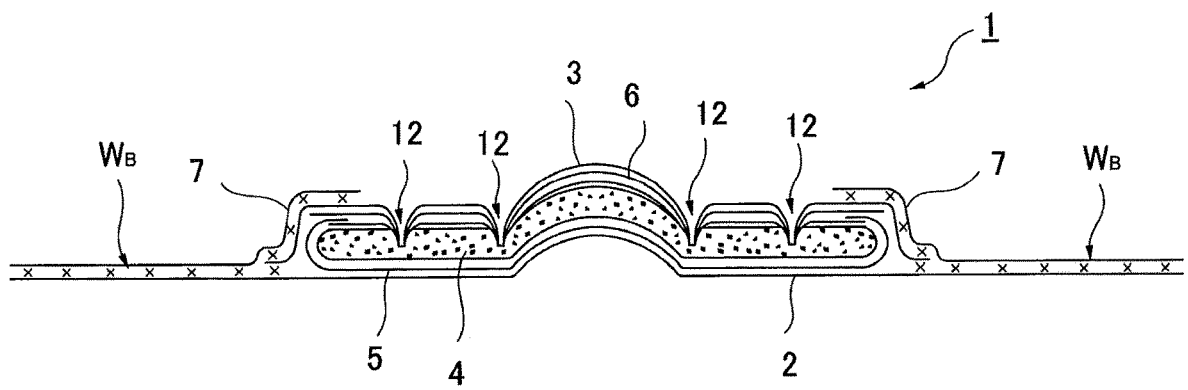
FIG. 4 is a cross-sectional view taken along a line IV-IV of FIG. 3.

As illustrated in FIG. 1, in the present sanitary napkin 1, a compressed groove base point 16, at which the compressed grooves constituting the first rear compressed groove 12 bilaterally and symmetrically formed on both sides of the center line CL in the lengthwise direction of the sanitary napkin 1 intersects with each other at a position corresponding to a front end 31 of the intergluteal cleft (see FIG. 3) of a wearer, is formed. In other words, the front end of the first rear compressed groove 12 (compressed groove base point 16) formed into the reverse heart shape in a planar view lies at the location that approximately coincides with the front end 31 of the intergluteal cleft of the wearer. As illustrated in FIG. 3, the front end 31 of the intergluteal cleft of the wearer means a position that buttock cleavage starts on the groin side, and is normally positioned at 50 to 90 mm distant rearward from the central part of the body fluid discharge part 32 although the position differs from person to person or differs depending on body types.

Moreover, as illustrated in FIG. 1, as to the outline of the sanitary napkin 1, at least an outline of a rear end of the napkin is formed into a symmetric wavelike shape in the width direction with respect to the center line CL in the lengthwise direction. The outline having the wavelike shape is formed by alternately arranging an outward convex curve and an inward convex curve, and inflection points where signs of curvatures change on the curve, lie at connection points of these curves. The inflection points are defined as outline inflection points 17. Because the above-mentioned outline is formed into the bilaterally symmetric wavelike shape, the outline inflection points 17 are provided by forming a right and left pair.

As illustrated in FIG. 1, the present sanitary napkin 1 includes easy deformation parts 18 that is caused by the compressed groove 10 and facilitates generation of a deformation in the transverse direction of the sanitary napkin 1 that has the above-mentioned compressed groove 10 as a base edge on or in the vicinity of two virtual lines S, S that connect the above-mentioned compressed groove base point 16 to the outline inflection points 17 on the right and left sides, respectively, while gradually increasing the distance between the two virtual lines S, S toward the outline inflection points 17. 17.

This configuration in the present sanitary napkin 1 allows a portion between the above-mentioned virtual lines S, S to convexly deform toward the skin side readily when being worn, and the convexly deformed portion fits the intergluteal cleft 30 and excels in wearing comfort. Because the above-mentioned compressed groove base point 16 provided at a position corresponding to the front end 31 of the intergluteal cleft of the wearer is formed at a front end of a region between the virtual lines S, S, the front end of the convexly deformed portion always corresponds to the front end 31 of the intergluteal cleft, and the fitness to the intergluteal cleft can be held preferably. In addition, because the outline inflection points 17 of the rear end, which is formed into the wavelike shape, of the napkin, are located at the rear end of the convexly deformable region between the above-mentioned virtual lines S, S, the convexly deformed region caused by an association of the compressed groove 10 with the outline of the sanitary napkin 1 can be clearly formed up to the rear end of the sanitary napkin 1. Furthermore, because the rear end of the convexly deformable region coincides with the outline inflection points 17, the deformation in which the outline inflection points 17 become the base point is likely to occur, and twists and wrinkles are unlikely to occur at the rear end in this region, which achieves wearing comfort.

Moreover, the above-mentioned virtual lines S, S are formed so as to gradually increase their distance from the above-mentioned compressed groove base point 16 toward the rear side. Hence, when the portion between the virtual lines S, S convexly deforms, as illustrated in FIG. 3, the portion fits the shape of the intergluteal cleft 30 that gradually widen from the front end 31 of the intergluteal cleft toward the rear side, thereby enhancing the fitness to the intergluteal cleft 30.

Figure 5:
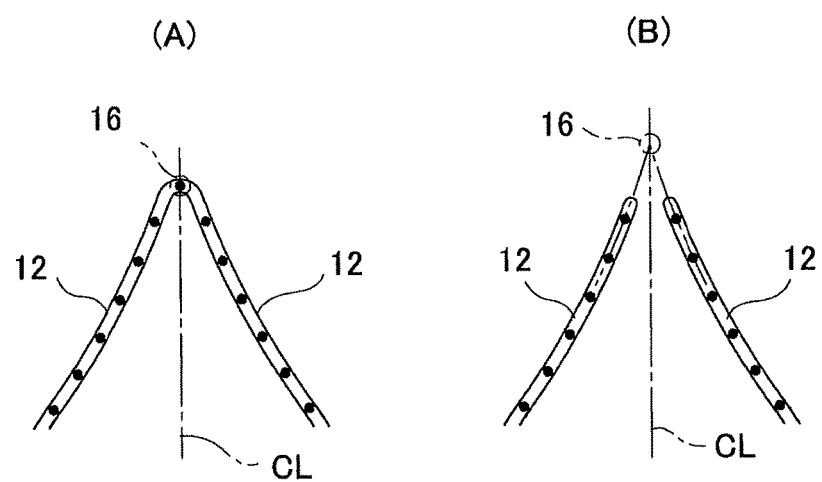
FIGS. 5(A) and (B) are planar views showing a compressed groove base point 16.

Further, a configuration of each part is described below in more detail. As illustrated in FIG. 5(A), when a front end of the above-mentioned first rear compressed groove is continuously formed on the center line CL in the lengthwise direction, the above-mentioned compressed groove base point 16 indicates a point where the right and left first rear compressed grooves 12, 12 intersect with each other on the center line CL in the lengthwise direction. As illustrated in FIG. 5(B), when front ends of the above-mentioned first rear compressed groove 12 are formed apart from each other on the center line Cl in the lengthwise direction, the above-mentioned compressed groove base point 16 indicates a point where center lines of the first rear compressed grooves 12, 12 on the right and left sides extended therefrom toward the front side intersect with each other on the center line CL in the lengthwise direction. The distance in the width direction of the napkin when the front ends of the first rear compressed grooves 12 are apart from each other is set at 10 mm or shorter, preferably set at 5 mm or shorter. When the distance is beyond 10 mm, the compressed point is unlikely to become the groove base point.

The above-mentioned compressed groove base point 16 may be formed of a compressed groove extending forward from the compressed groove base point 16, but is preferably formed of a compressed groove extending rearward from the compressed groove base point 16. Thus, a deformation in the transverse direction is likely to occur in a region on the rear side of the compressed grove point 16.

The above-mentioned compressed groove base point 16 is preferably arranged at a position where a distance L from the center of the body fluid discharge part corresponding region H, or a distance L from the center of a length in a front and back direction of a base edge of a wing-shaped flap W provided on both sides of and corresponding to the body discharge part 32 of the wearer, is about 50 to about 100 mm. By arranging the above-mentioned compressed groove base point 16 in this range, the above-mentioned compressed groove base point 16 is provided at a position corresponding to the front end 31 of intergluteal cleft. Here, this range approximately coincides with a length from the central part of the body fluid discharge part 32 of the wearer to the front end 31 of the intergluteal cleft.

The above-mentioned first rear compressed groove 12 has the above-mentioned compressed groove base point 16 as its front end, extends from this compressed groove base point 16 obliquely rearward on both sides, curves at the rear end parts toward the center line CL in the lengthwise direction, separates from each other toward the right and left on the center line CL in the lengthwise direction, and is formed as an approximately heart shape in a planar view.

Figure 6:
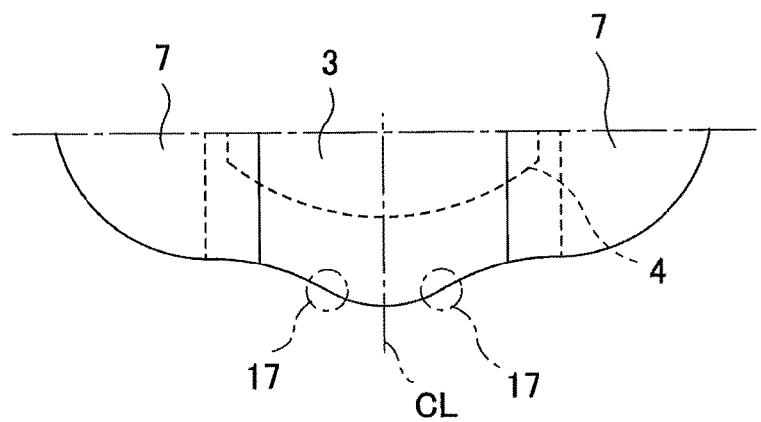
FIG. 6 is a planar view illustrating an outline of a rear end.

In contrast, as illustrated in FIG. 1 and FIG. 6, the outline of the above-mentioned rear end formed into a bilaterally symmetric wavelike shape is formed into a wavelike shape with a dimension including at least a single pair, preferably one to three pairs, and further preferably a pair of inflected points within the width of the absorbent body 4. This wavelike-shaped outline is preferably arranged so that a peak of a convex outward curve is positioned on the center line CL in the lengthwise direction. Thus, with respect to the transverse direction of the sanitary napkin 1, the deformation in which the central part in the width direction protrudes toward the skin side, is likely to occur.

As illustrated in FIG. 1, the range where the outline of the sanitary napkin 1 is formed into the wavelike shape, is preferably continuously provided from the outline of the rear end of the sanitary napkin 1 to the rear portions of the outline on both sides. Thus, twists and curls of the rear flap $W_B$ when being worn can be prevented, and the waring comfort can be enhanced. In contrast, the outline of the above-mentioned wavelike shape may be formed only at the rear end of the sanitary napkin 1, and the outline of the other portion may be formed of straight lines and curved lines. In the example illustrated in FIG. 1, the outline of the front end of the main part and the front-side outline of the wing-shaped flap are formed of the wavelike shape, respectively, but these outlines may be formed of straight lines and curved lines. Moreover, the other outlines are approximately formed of straight lines, but the outlines may be formed of wavelike lines, curved lines or a combination thereof.

Figure 7:
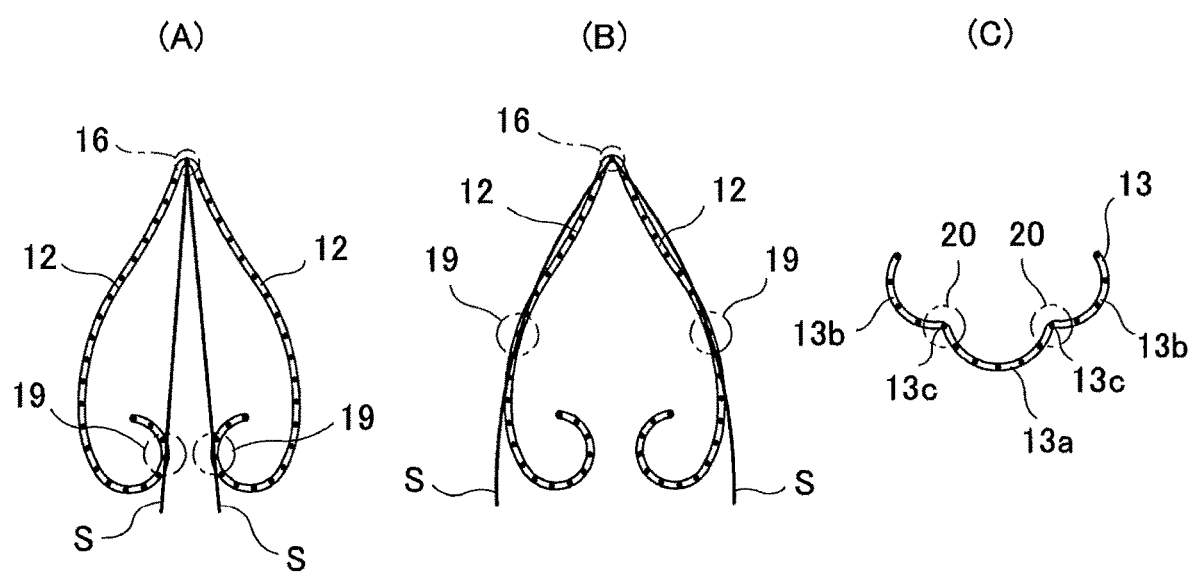
FIGS. 7(A) through (C) are planar views showing a readily deformation part 18.

Next, the above-mentioned virtual line S may be formed as a straight line as illustrated in FIG. 1 and FIG. 7(A), or may be formed as a curved line convexly outward or inward (outward in the example of the drawing) in the width direction as illustrated in FIG. 7(B). When the virtual lines S are formed of curve lines, the maximum distance between a straight line connecting both ends of the virtual lines S with each other (straight line connecting the compressed groove base point 16 to the outline inflection points 17) and the virtual line S is set at 10 mm or shorter, preferably set at 7 mm or shorter. When the maximum distance is longer than 10 mm, the deformation in the transverse direction in which the compressed groove 10 is made the base edge is unlikely to occur, which is liable to decrease the fitness to the intergluteal cleft 30.

The distance between the virtual lines S, S on the right and left sides is provided to gradually increase from the compressed groove base point 16 toward the rear side. Thus, because the deformation of the sanitary napkin 1 in the transverse direction in which the virtual line S is made the base edge gradually widens toward the rear side of the sanitary napkin 1, the sanitary napkin fits the shape of the intergluteal cleft 30, thereby further improving the fitness to the intergluteal cleft 30.

An angle α between the virtual lines S, S on the right and left sides is preferably set at 10 to 30°. When the above-mentioned virtual lines S are formed of curved lines, the above-mentioned angle only has to be set at an angle between straight lines connecting the compressed groove base point 16 to the outline inflection points 17. By forming the virtual lines S, S on the right and left sides in this angle range, the sanitary napkin fits the shape of the intergluteal cleft 30, and the fitness to the intergluteal cleft 30 can be further improved.

Next, the above-mentioned easy deformation part 18 is described below. The above-mentioned easy deformation part 18 is part of the compressed grove 10 that becomes a base point of the deformation of the sanitary napkin 1 such as a protruding portion and a changing portion of the compressed groove in order to facilitate the deformation in the transverse direction of the sanitary napkin 1 in which the above-mentioned compressed groove 10 is made a base edge. By arranging the easy deformation parts 18 on the above-mentioned virtual line S or the vicinity thereof, the deformation of the sanitary napkin in the transverse direction along the above-mentioned virtual line S readily occurs.

The above-mentioned easy deformation parts 18 can be formed in a variety of forms. For example, as illustrated in FIG. 7(A), (B), the easy deformation parts 18 may be formed of contact points 19 of the above-mentioned virtual lines S that form tangent lines or touching lines to the first rear compressed groove 12 formed of a curved line, or may be formed of curvature changing points 20 that changes the curvature of a second rear compressed groove 13 formed of a curved line, as illustrated in FIG. 7(c).

The above-mentioned contact points 19, as illustrated in FIG. 7(A), may be provided at positions that touch the virtual lines S passing the inside of the first rear compressed groove 12, or may be provided at positions that touch the virtual lines S passing the outside of the first rear compressed groove 12 as illustrated in FIG. 7(B).

The curvature changing points 20 are points where the curvature sharply increases (curvature radius of the curved line significantly decreases) in the compressed groove 10 formed of a combination of curved lines having a plurality of curvatures, and are preferably formed so that the curvature sharply changes fivefold or more, preferably about fivefold to about tenfold. In the example illustrated in FIG. 7(C), the above-mentioned second rear compressed groove 13 is composed of an arc 13*a* that is convexly curved rearward on the center line CL in the lengthwise direction, arcs 13*b*, 13*b* that are convexly curved obliquely rearward on both sides thereof, and arcs 13*c*, 13*c* that project forward while connecting the arc 13*a* to the arcs 13*b*. Moreover, the above-mentioned curvature changing points 20 are formed of the arcs 13*c* projecting forward and having the curvatures greater than those of the arcs 13*a*, 13*b* that are convexly curved rearward. Like the above-mentioned second rear compressed groove 13, when having the compressed groove part crossing the virtual lines S, S on the right and left sides, if the compressed groove in the crossing portions is formed of a straight line along the width direction of the sanitary napkin 1, the deformation between the virtual lines S, S in the transverse direction of the sanitary napkin is unlikely to protrude so as to form a convex chevron, which is not preferable. As illustrated in FIG. 1, the compressed grooves are preferably formed of curved lines that are convexly curved rearward or forward in the lengthwise direction of the sanitary napkin 1, preferably curved lines that are convexly curved rearward.

The above-mentioned easy deformation part 18 is preferably present in a strip-shaped range that has a width of 3 mm from the virtual lines S, which is made the center, on each side. Even if the above-mentioned easy deformation part 18 is not accurately present on the virtual lines S, the above-mentioned effect can be obtained as long as the easy deformation part 18 is present in a certain range. However, a groove present more than 3 mm apart from the virtual lines S is not the easy deformation part because the groove does not contribute to the deformation in the transverse direction along the virtual lines S.

Only a single pair of the easy deformation parts 18 may be present in an intermediate position of the virtual lines S, or a plurality of pairs of the easy deformation parts 18 may be present at intervals in a direction along the above-mentioned virtual lines S. In particular, when a so-called daytime napkin that covers only a range close to the groin of the buttock and has a total length shorter than 30 cm is used, the easy deformation parts 18 are made one to three pairs, preferably one to two pairs. When a so-called nighttime napkin that is formed extending long rearward so as to cover a wide range of buttocks and has a total length of 30 cm or more is used, two to seven pairs of the easy deformation parts 18 only have to be provided, preferably two to four pairs.

The above-mentioned easy deformation part 18 is preferably formed as dots along the virtual lines S, and when the easy deformation part is formed of linear compressed grooves along the virtual lines S, the deformation in the transverse direction is likely to occur, which is not preferable because the deformation in the front and rear direction is unlikely to occur.

Example of Other Embodiments

In the above-mentioned embodiments, although an example of a so-called nighttime napkin that covers a wide range of buttocks of a wearer and extends long rearward has been described, the embodiments can be applied similarly to a so-called daytime napkin that covers only a range close to a groin of the buttocks.

A variety of aspects in the embodiments of the present invention is added below.

(Clause 1)

According to a first aspect, an absorbent article in which an absorbent body is interposed between a liquid permeable topsheet and a backsheet and compressed grooves recessed toward the backsheet are formed in a surface of the liquid permeable topsheet, is provided, wherein a compressed groove base point where the compressed grooves bilaterally and symmetrically formed on both sides of a center line in a lengthwise direction of the absorbent article, or lines extended from center lines of the compressed grooves, intersect with each other at a position corresponding to a front end 31 of a intergluteal cleft of a wearer, is formed, and a pair of outline inflection points is formed on the right and left sides in an outline of a rear end of the absorbent article formed into a bilaterally symmetric wavelike shape, and wherein an easy deformation part that facilitates a deformation in a transverse direction of the absorbent article and is formed of the compressed grooves that become base edges of the deformation, is present on or in the vicinity of two virtual lines that connect the compressed base point to the outline inflection points on right and left sides, respectively, such that a distance between the two virtual lines gradually increases toward a rear side.

In the first aspect, the compressed grove base point where the compressed grooves formed bilaterally and symmetrically on both sides of the center line in the lengthwise direction of the absorbent article, or the lines extended from the center lines of the compressed grooves intersect with each other at the position corresponding to the front end of the intergluteal cleft of the wearer, is formed, and the right and left pair of the outline inflection points is formed in the outline of the rear end of the absorbent article formed in the bilaterally symmetric wavelike shape. Then, the easy deformation part that facilitates the deformation in the transverse direction of the absorbent article and is formed of the compressed grooves that become the base edge of the deformation, is present on or in the vicinity of the two virtual lines that connect the compressed base point to the outline inflection points on the right and left sides, respectively, such that a distance between the two virtual lines gradually increases toward the rear side. Because of this, a portion between the virtual lines is likely to deform so as to protrude toward a skin side when being worn, and the convexly deformed portion fits the intergluteal cleft, which excels in wearing comfort. Because the compressed groove points provided at positions corresponding to the front end of the intergluteal cleft of the wearer are formed at a front end of a convexly deformable region provided between the virtual lines, the front end of the convexly deformed region always corresponds to the front end of the intergluteal cleft, thereby preferably retaining fitness to the intergluteal cleft. Moreover, because the outline curvature points of the rear end of the absorbent article formed in the wavelike shape are positioned at the rear end of the region that convexly deforms and is provided between the virtual lines, the region that convexly deforms by associating the compressed grooves with the outline of the absorbent article can be clearly formed up to the rear end of the absorbent article. Furthermore, because the rear end of the region that convexly deforms corresponds to the outline inflection points, the rear end part of this region is unlikely to have twists or wrinkles, thereby improving wearing comfort.

Further, because the above-mentioned virtual lines are formed so as to increase their distance from the compressed groove point toward the rear side, the absorbent article is likely to fit a shape of the intergluteal cleft when the region between the virtual lines is convexly deformed, which improves the fitness to the intergluteal cleft.

(Clause 2)

As a second aspect, the absorbent article according to the first aspect is provided, wherein the easy deformation part is formed of a contact point at which the virtual lines form tangent lines or touching lines to the compressed grooves formed of curved lines or curvature changing points of the compressed grooves formed of curved lines.

In the second aspect, because the easy deformation part formed of the compressed grooves is constituted of the contact points at which the virtual lines form the tangent lines or the touching lines to the compressed grooves formed of the curved lines or the curvature changing points of the compressed grooves formed of the curved lines, the deformation in the transverse direction of the absorbent article having the compressed grooves as base edges is likely to occur.

(Clause 3)

As a third aspect, the absorbent article according to the first or second aspect is provided, wherein the easy deformation part is present in a strip-shaped range that has a width of 3 mm in a direction normal to the virtual lines, which is made the center, on each side thereof.

In the third aspect according to the above-mentioned embodiment, the easy deformation part is present in the strip-shaped range having a certain width. By providing the easy deformation part in this certain range, the above-mentioned effect can be obtained.

(Clause 4)

As a fourth aspect, the absorbent article according to any one of the first to third aspects is provided, wherein a pair of easy deformation parts is present, or a plurality pairs of the easy deformation parts are present along the virtual line.

In the above-mentioned fourth aspect, only a pair of the easy deformation parts may be present, or a plurality pairs of the easy deformation parts may be present at intervals along the virtual line. In particular, when the absorbent article is formed as a so-called nighttime napkin formed extending long rearward so as to cover a wide range of buttocks and having a total length of 30 cm or more, multiple pairs, two or more pairs of the compressed groove changing points are preferably present to readily generate the deformation along the virtual lines.

(Clause 5)

As a fifth aspect, the absorbent article according to any one of the first to fourth aspect is provided, wherein the virtual lines if formed of straight lines or curved lines that are convexly curved outward or inward in a width direction.

In the fifth aspect, the virtual lines are formed of the straight lines or the curved lines that are convexly curved outward or inward to improve fitness to intergluteal cleft.

(Clause 6)

As a sixth aspect, the absorbent article according to any one of the first to fifth aspects is provided, wherein an angle between the virtual lines on the right and left sides is 10 to 30°.

In the sixth aspect, the angle between the virtual lines on the right and left sides is made 10 to 30° to cause the convexly deformable portion between the virtual lines to readily fit the intergluteal cleft.

As a seventh aspect, the absorbent article according to any one of the first to sixth aspects is provided, wherein the compressed grooves on the right and left sides are arranged so as to be coupled to or apart from each other on a center line in a lengthwise direction at the compressed groove base point.

In the seventh aspect, the compressed grooves on the right and left sides may be coupled to or apart from each other on the center line in the lengthwise direction at the compressed groove base point. When the compressed parts on the right and left sides are coupled to each other, a part where the compressed grooves intersect with each other forms the compressed groove base point, and when the compressed parts on the right and left sides are arranged apart from each other, a part where lines extended from center lines of the compressed grooves intersect with each other forms the compressed groove base point.

As discussed above, although the present invention has been described according to the embodiments, the present invention is not limited to the above-discussed embodiments, and various modifications can be made within the scope of claims.

The present application is based upon and claims priority of Japanese Patent Application No. 2016-11996 filed on Jan. 26, 2016, with Japanese Patent Office, the entire contents of which are hereby incorporated herein by reference.

DESCRIPTION OF REFERENCE SYMBOLS 1 sanitary napkin
2 liquid impermeable backsheet
3 liquid permeable topsheet
4 absorbent body 5 encapsulating sheet
6 second sheet
7 side non-woven fabric
10 compressed groove
11 central compressed groove
12 first rear compressed groove
13 first rear compressed groove
14 first front compressed groove
15 second front compressed groove
16 compressed groove base point
17 outline inflection point
18 easy deformation part
19 contact point
20 curvature changing point
CL lengthwise direction center line
W wing-shaped flap
$W_B$ rear flap

The invention claimed is:

1. An absorbent article comprising:
a liquid permeable topsheet having compressed grooves in a surface;
a backsheet; and
an absorbent body interposed between the liquid permeable topsheet and the backsheet,
wherein a compressed groove base point where at least one first compressed groove among the compressed grooves formed bilaterally and symmetrically on both sides of a center line in a lengthwise direction of the absorbent article or lines extended from center lines of the at least one first compressed groove, intersects with each other at a position corresponding to a front end of an intergluteal cleft of a wearer is formed, and a right and left pair of outline inflection points is formed in an outline of a rear end of the absorbent article, the outline of the rear end being formed into a bilateral and symmetric wavelike shape formed by alternately arranging a backward protruding curve and a forward protruding curve, the inflection points lying at connection points of the backward protruding curve and the forward protruding curve, signs of curvature of the outline changing at the inflection points, and
wherein a second compressed groove that facilitates generation of a deformation in a transverse direction of the absorbent article and that becomes a base edge of the deformation, is provided on or in the vicinity of two virtual lines connecting the compressed groove base point to the outline inflection points on right and left sides, respectively, the inflection points lying at connection points of the backward protruding curve and the forward protruding curve, the outline inflection points being points at which the signs of curvature of the outline changing, such that a distance between the two virtual lines gradually increases toward a rear side and between the at least one first compressed groove and the outline inflection point, and
wherein the second compressed groove includes a center arc that curves rearward on the center line in the lengthwise direction and side arcs that obliquely curve rearward on both sides of the center arc, and the each of the side arcs overlaps with the forward protruding curve of the outline of the rear end in the lengthwise direction.

2. The absorbent article according to claim 1, wherein the second compressed groove is formed of contact points of tangent lines or touching lines that are the virtual lines to the compressed groves formed of curved lines or curvature changing points of the compressed grooves formed of the curved lines.

3. The absorbent article according to claim 1, wherein the second compressed groove is present in a strip-shaped range having a width of 3 mm in a direction normal to each of the virtual lines on each side of each of the virtual lines each of which is made a center.

4. The absorbent article according to claim 1, wherein each of the virtual lines is formed of a straight line or a curved line that is convexly curved outward or inward in a width direction.

5. The absorbent article according to claim 1, wherein an angle between the virtual lines on the right and left sides is 10 to 30°.

6. The absorbent article according to claim 1, wherein the compressed grooves on the right and left sides are, arranged so as to be coupled with each other or to be apart from each other on the center line in the lengthwise direction.

* * * * *